United States Patent [19]

Witte

[11] Patent Number: 5,027,303

[45] Date of Patent: Jun. 25, 1991

[54] MEASURING APPARATUS FOR PEDAL-CRANK ASSEMBLY

[76] Inventor: Don C. Witte, 155 Logan Mill Road, Boulder, Colo. 80302

[21] Appl. No.: 381,110

[22] Filed: Jul. 17, 1989

[51] Int. Cl.⁵ .......................... G01L 5/02; A61B 5/02
[52] U.S. Cl. .................................... 364/511; 364/550; 364/413.04; 272/73; 73/862.08; 73/862.36
[58] Field of Search .................. 364/511, 550, 551.01, 364/506, 413.03, 413.04; 73/862.08, 862.36, 862.38, 862.68; 272/73

[56] References Cited

U.S. PATENT DOCUMENTS

| | | | |
|---|---|---|---|
| 3,984,666 | 10/1976 | Barron | 364/506 |
| 4,141,245 | 2/1979 | Brandstetter | 73/144 |
| 4,141,248 | 2/1979 | Bargenda | 73/379 |
| 4,244,021 | 1/1981 | Chiles, III | 364/413 |
| 4,358,105 | 11/1982 | Sweeney, Jr. | 364/413.04 |
| 4,434,801 | 3/1984 | Jiminez et al. | 364/413.04 |
| 4,463,433 | 7/1984 | Hull et al. | 364/506 |
| 4,634,433 | 7/1984 | Hull et al. | 364/506 |
| 4,811,238 | 3/1989 | Gerrath et al. | 364/511 |
| 4,907,168 | 3/1990 | Boggs | 364/506 |

OTHER PUBLICATIONS

2/26/68, M. J. A. J. M. Hoes et al., "Measurement of Forces Exerted on Pedal and Crank During Work on a Bicycle Ergometer at Different Loads", Int. Z. angew. Physiol. einschl. Arbeitsphysiol., pp. 26 and 33–42.

Peter Cavanagh, David Sanderson, The Pennsylvania State University, "The Biomechanics of Cycling: Studies of the Pedaling Mechanics of Elite Pursuit Riders," pp. 91–122.

Primary Examiner—Parshotam S. Lall
Assistant Examiner—Brian M. Mattson

[57] ABSTRACT

Apparatus measures output parameters including torque, work, power, rpm and time for selected rotations of the user of a power-using device having a pedal-crank assembly. Torque vs. angular position values are input from rotating strain gauges and angular position sensors to a programmed microprocessor which stores and processes this data. An approximate-integration algorithm produces a value for work produced over a selected rotation. This work value is further divided by the time interval to produce a value for the instantaneous power being produced. With appropriate sensors, many forms of data for both right and left crank arms can be displayed and/or stored separately.

30 Claims, 8 Drawing Sheets

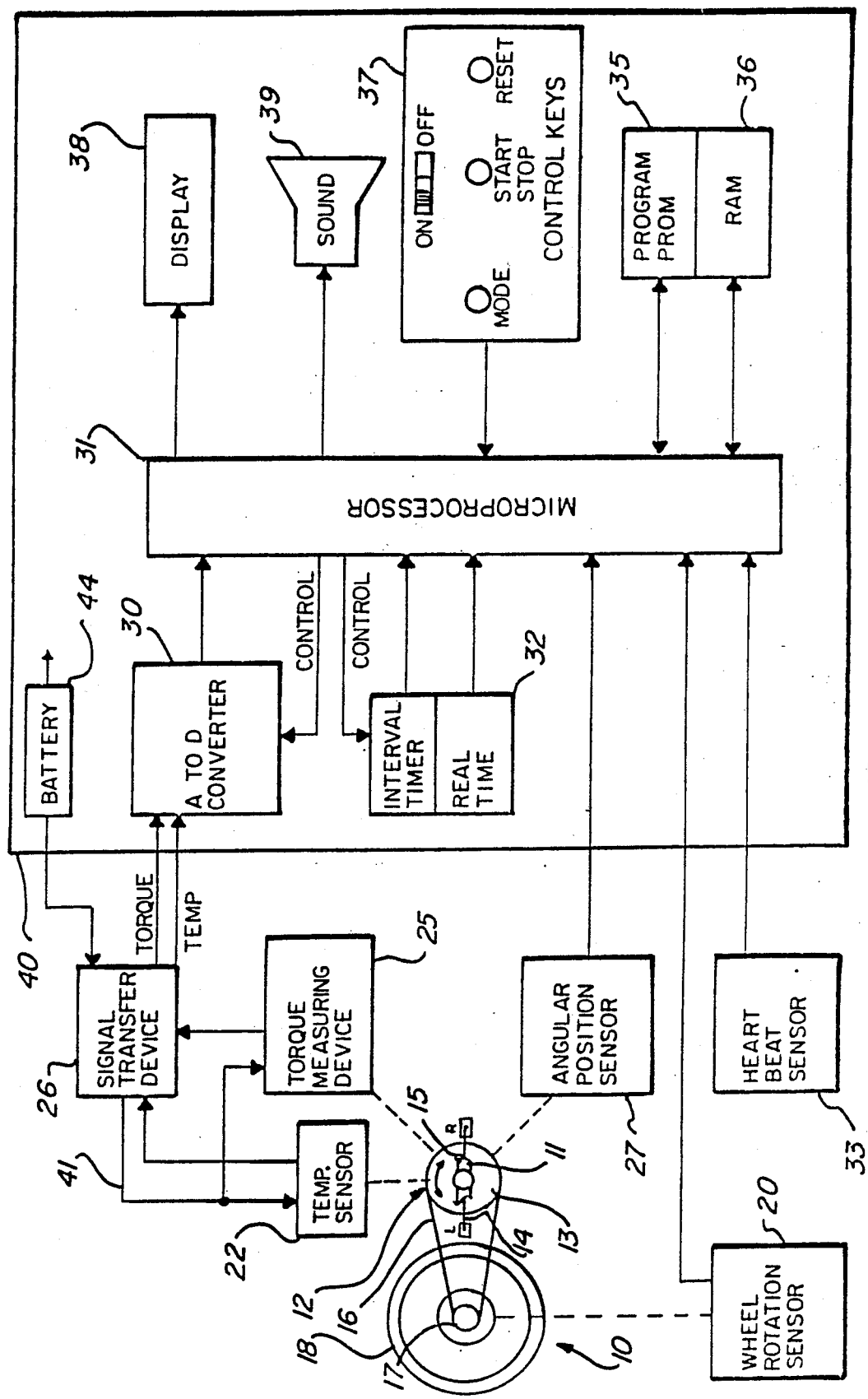
Fig_1

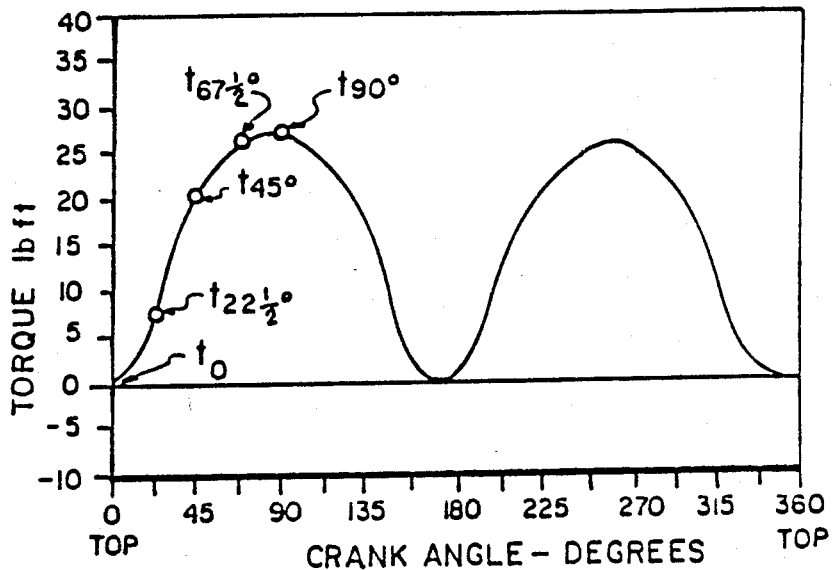
Fig_4
TYP. TORQUE VS CRANK ANGLE RESULTANT OF LEFT + RIGHT LEGS
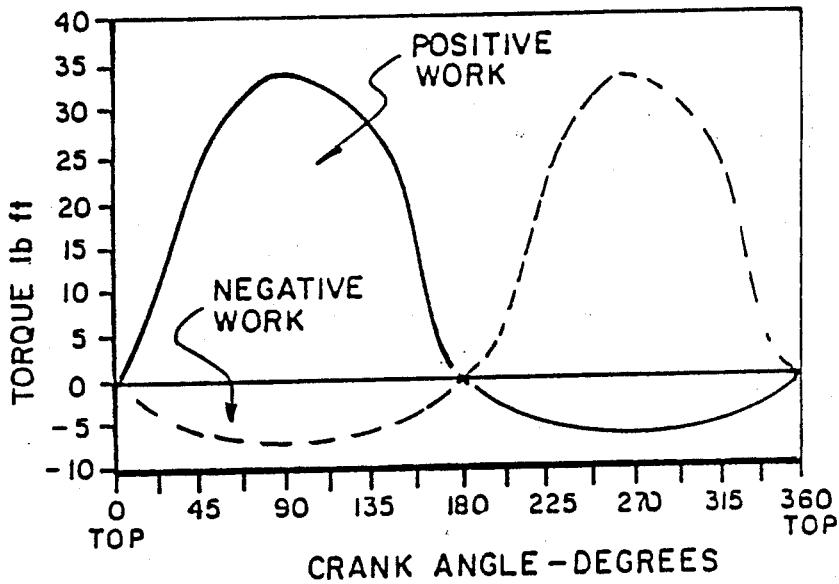
Fig_5
TYP. TORQUE VS CRANK ANGLE
RIGHT LEG = ──
LEFT LEG = ─ ─ ─
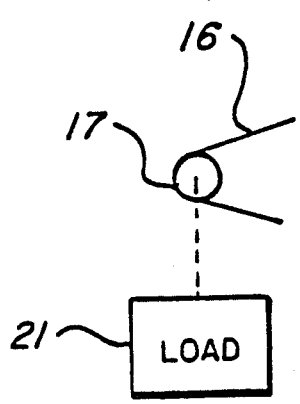
Fig_2

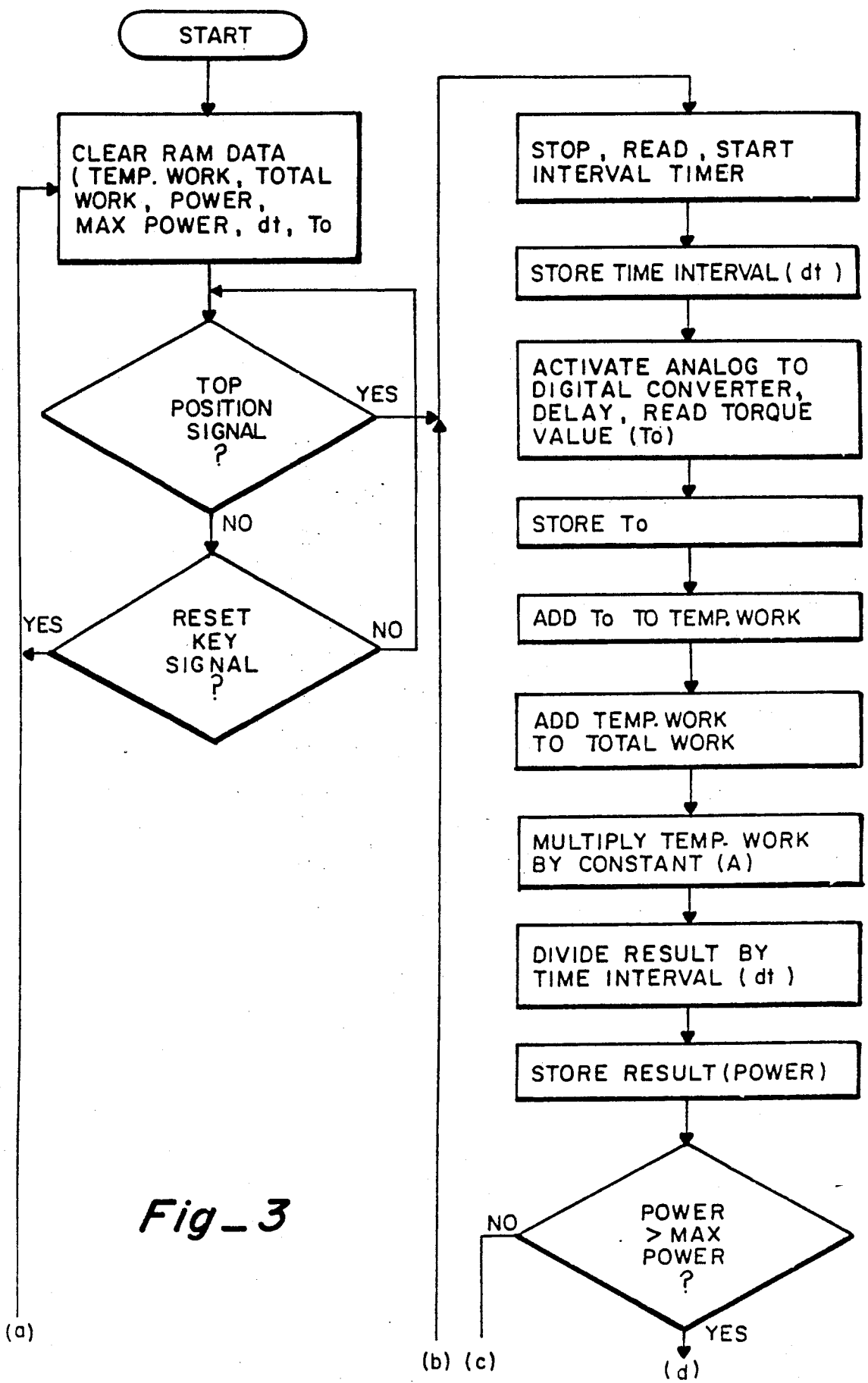
Fig_3

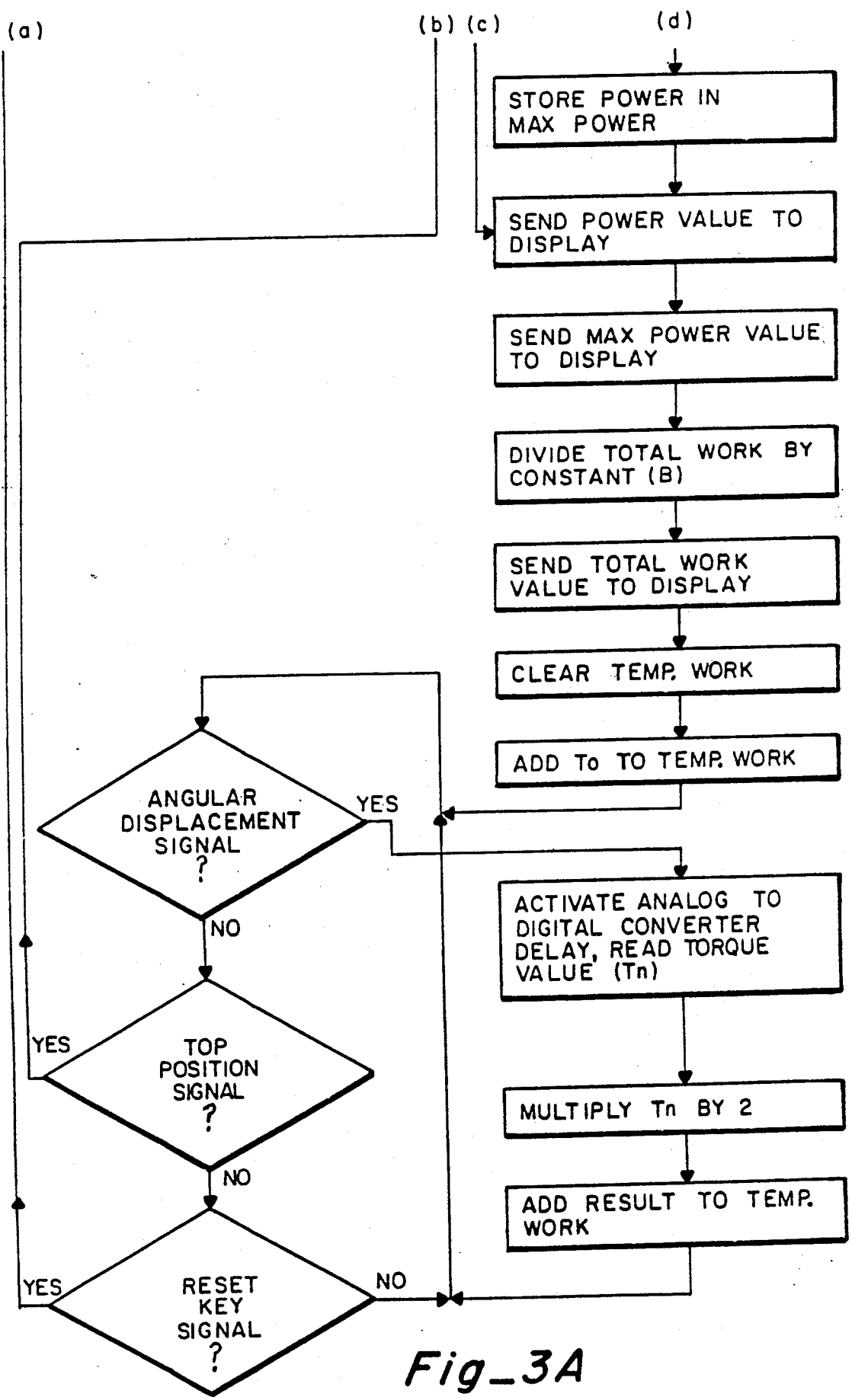
Fig_3A

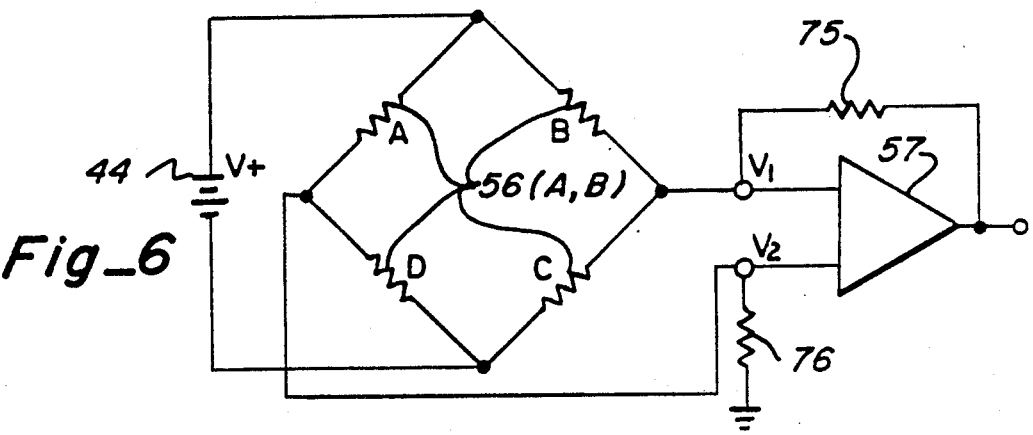
Fig_6
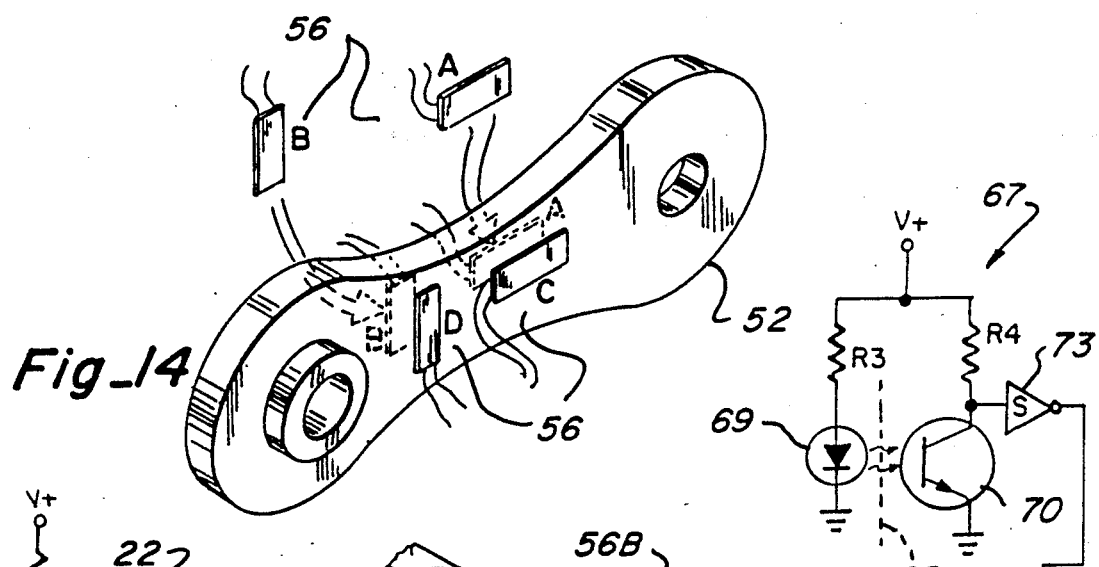
Fig_14
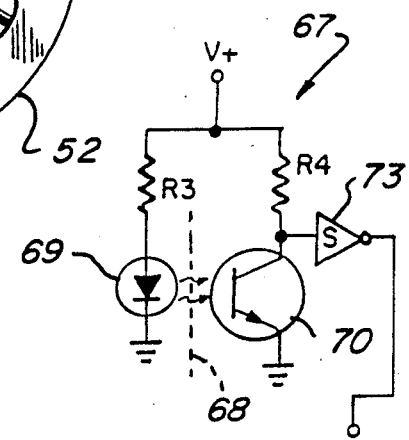
Fig_18
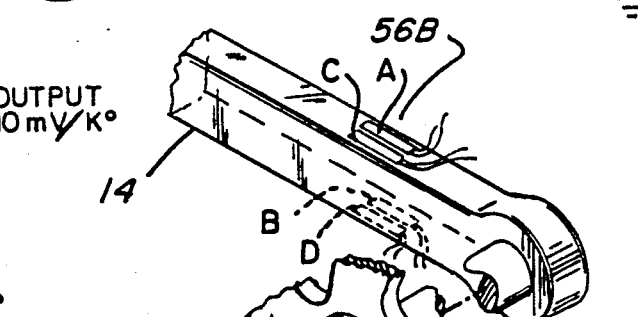
Fig_16
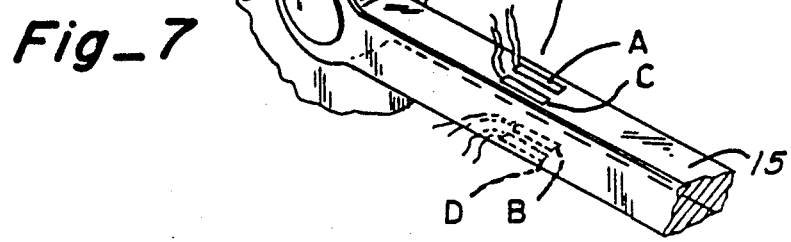
Fig_7

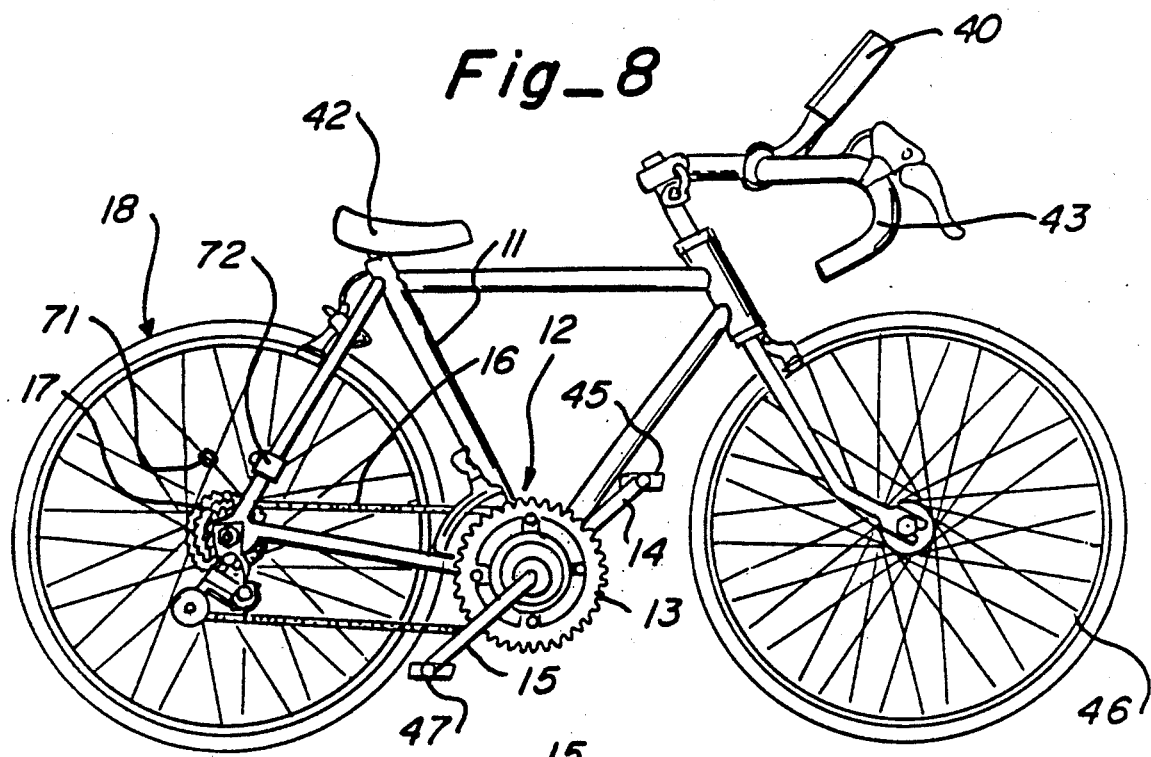
Fig_8
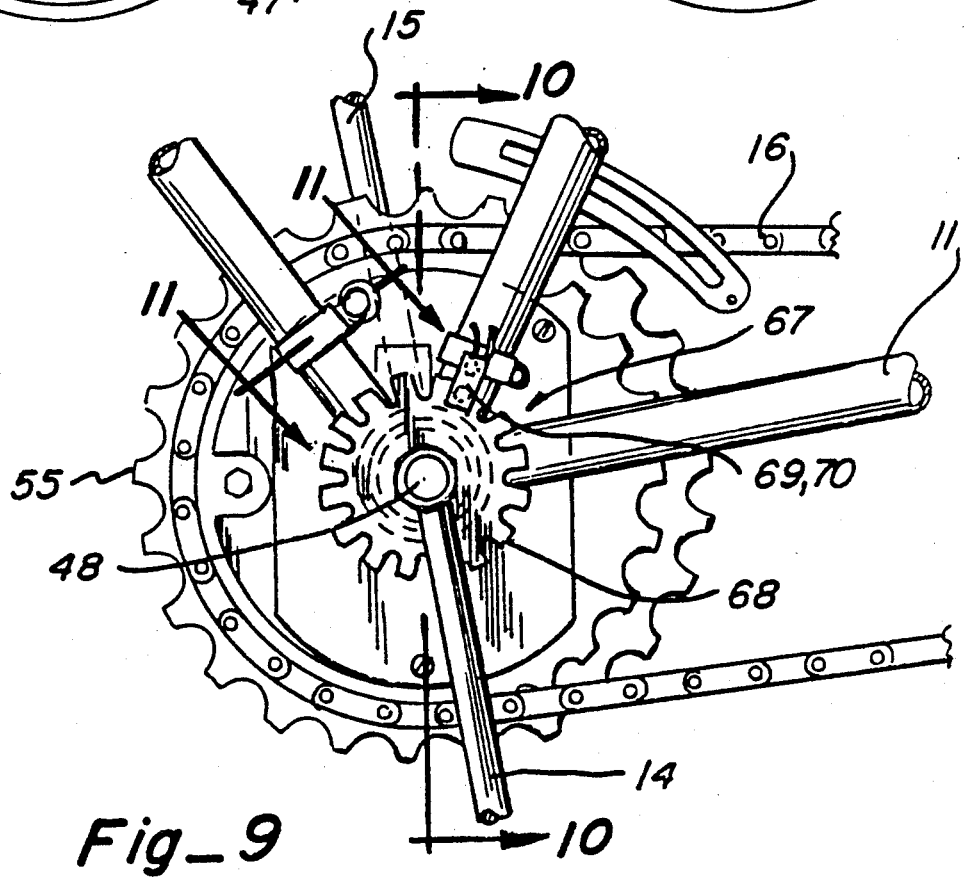
Fig_9

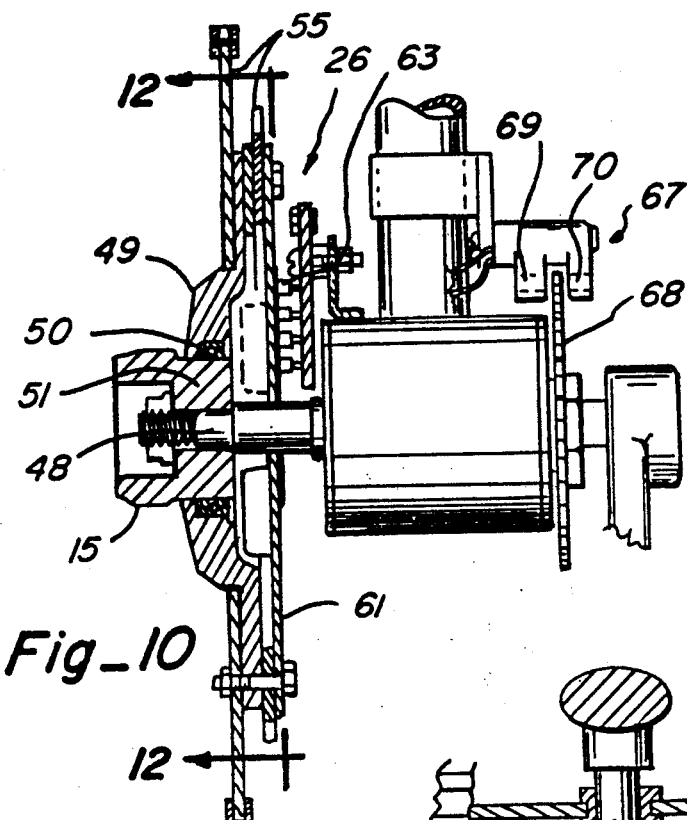
Fig_10
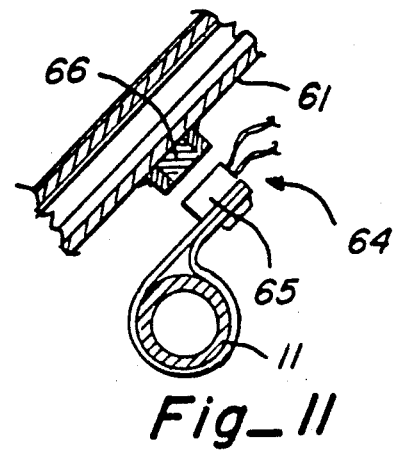
Fig_11
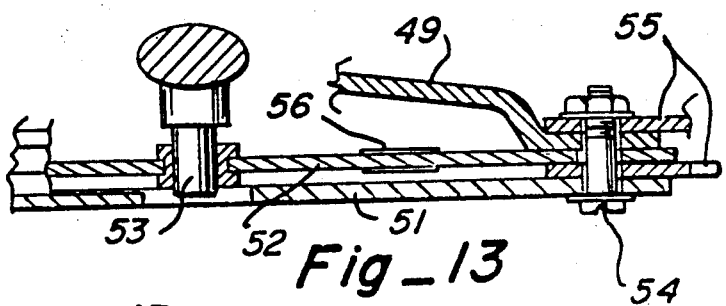
Fig_13
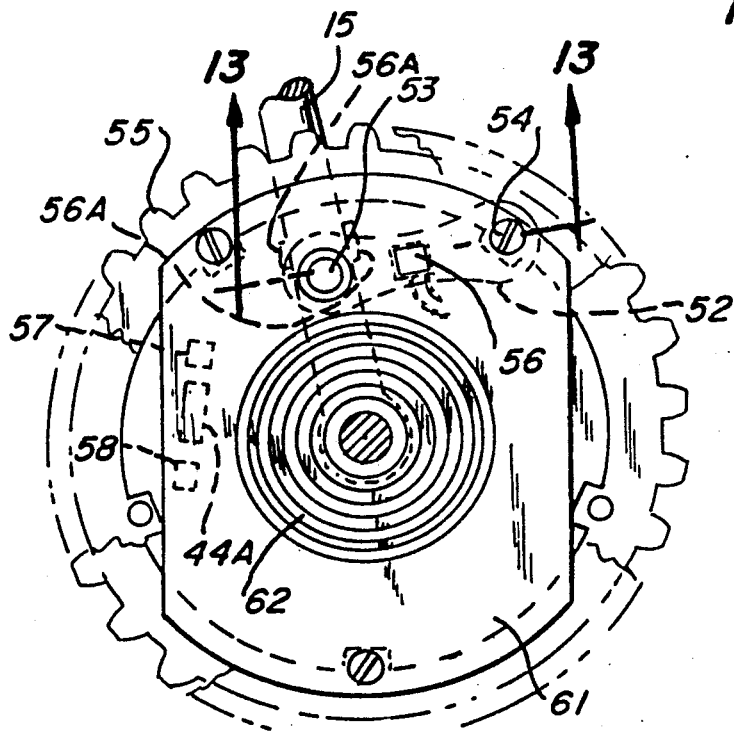
Fig_12

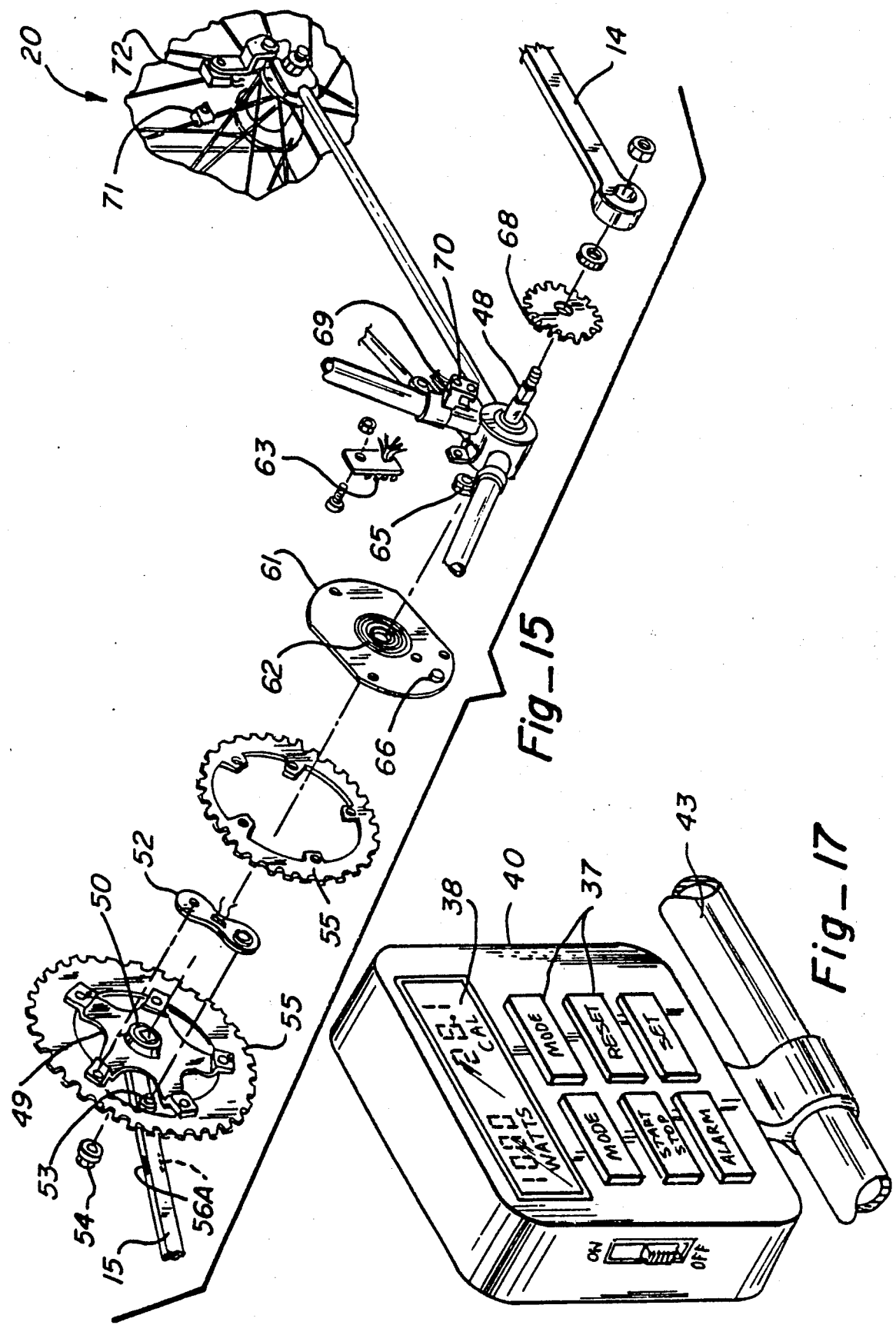

1

MEASURING APPARATUS FOR PEDAL-CRANK ASSEMBLY

TECHNICAL FIELD

This invention relates to a novel and improved apparatus for measuring a variety of output parameters of the user of a power-using device having a pedal-crank assembly.

BACKGROUND ART

There is a need for a measuring apparatus that will indicate a variety of output parameters of a user of any power-using device having a pedal-crank assembly, whether stationary or movable. Prior attempts to measure various output parameters of the user have been made primarily on stationary pedal-crank assemblies in the form of stationary exercise bicycles or ergometers. Stationary bicycles require a means to apply an artificial work load, such as a friction brake, an electric generator, or a constant-speed electric motor to simulate a range of load conditions. These work load devices control the torque and power the user must produce. The torque and power required for a user riding a bicycle along a road, however, are determined by the user by the choices of the gearing and speed, but also are affected by many factors such as: the mechanical condition of the bicycle, the condition of the road surface, the slope of the road, the total weight of the user plus bicycle and load, the wind speed and direction, and the acceleration. No matter what combinations of the above factors apply, parameters such as torque, power and work can now be displayed instantaneously to the user of any pedal-crank assembly.

M.J.A.J.M. Hoes et al. in a publication in Int. Z. angew, Physiol. einschl. Arbeitsphysiol. entitled "Measurement of Forces Exerted on Pedal and Crank During Work" discusses the results of force measurements on the pedal and crank at different angular positions.

Bargenda, U.S. Pat. No. 4,141,248, discloses an ergometer with a generator which can be controlled to provide a constant, preset power load. The product of a tachometer signal, which is proportional to the rotational speed, and the average torque, which is determined from an integrator circuit connected to a series circuit of two strain gauges with one mounted on each crank arm, provides a signal that when compared to another preset signal determines the control voltage going to the generator.

Chiles, U.S. Pat. No. 4,244,021, discloses an exerciser using a work generator coupled to the pedal assembly and wherein a programmed microprocessor is used to provide a constant power selected by the user and to provide data concerning the work done and heart rate.

Hull et al, U.S. Pat. No. 463,433, discloses a means for indicating the pedaling efficiency of a user by using strain gauges mounted on a single bicycle pedal in order to determine the ratio of force exerted perpendicular to the crank arm and force exerted parallel to the crank arm. On the road use and biofeedback are emphasized.

Brandstetter, U.S. Pat. No. 4,141,245, discloses a device for determining work and power by measuring the force of a flexible chain drive and multiplying that value by a measured value of the distance or of the speed. Use on a bicycle or motorcycle is discussed.

Chapter 5 of *Science of Cycling*, edited by Edmund R. Burke, discusses a variety of studies of biomechanical parameters which have been done on stationary ergometers.

DISCLOSURE OF THE INVENTION

Measuring apparatus for measuring a variety of output parameters of a user of a power-using device having a pedal-crank assembly includes torque measuring means and crank arm angular position sensing means providing data signals that are input into a programmed microprocessor which stores and processes same. A timer provides timing signals for the microprocessor. An approximate-integration algorithm in the microprocessor program is used to calculate a value for the work produced by the user over each selected angular displacement of the crank assembly. The work value is divided by the time interval to provide a value for the instantaneous power produced. Data for both the left and right crank arms can be determined separately and displayed and/or stored as desired. Signals from a wheel rotation sensor, a heartbeat sensor and a temperature sensor are also input into the microprocessor t provide additional data. A readout device displays data values output from the microprocessor.

BRIEF DESCRIPTION OF THE DRAWINGS

Details of this invention are described in connection with the accompanying drawings in which like parts bear similar reference numerals and in which:

FIG. 1 is a schematic diagram of the measuring apparatus for a moving bicycle embodying features of the present invention.

FIG. 2 is a schematic diagram showing the modification of the measuring apparatus of FIG. 1 for a stationary bicycle or ergometer.

FIGS. 3 and 3A are a flowchart for the program for the microprocessor shown in FIG. 1.

FIG. 4 is a curve showing a typical series of torque values (y-axis) of the net resultant of both left and right legs taken over one complete revolution at 22.5 degree intervals.

FIG. 5 is a curve showing typical torque values for right and left legs measured separately.

FIG. 6 is a schematic diagram of a strain gauge circuit.

FIG. 7 is a perspective view of the crank arms with an alternative arrangement of the strain gauges.

FIG. 8 is a right side elevation view of a movable bicycle having mounted thereon measuring apparatus according to the present invention.

FIG. 9 is an enlarged left side elevation of the pedal-crank assembly shown in FIG. 8.

FIG. 10 is a sectional view taken along lines 10—10 of FIG. 9.

FIG. 11 is a sectional view taken along lines 11—11 of FIG. 9.

FIG. 12 is a sectional view taken along lines 12—12 of FIG. 10.

FIG. 13 is a sectional view taken along lines 13—13 of FIG. 12.

FIG. 14 is a perspective view of the torque link.

FIG. 15 is an exploded view of the pedal-crank assembly shown in FIGS. 8-14.

FIG. 16 is an electric circuit diagram of the temperature sensor 22 shown in FIG. 12.

FIG. 17 is a front perspective view of the housing shown in FIG. 8.

FIG. 18 is an electric circuit diagram of the second angular position sensor 67 shown in FIG. 10.

DETAILED DESCRIPTION

Referring now to FIG. 1, there is shown a schematic block diagram of measuring apparatus embodying features of the present invention. In general, there is a power-using device 10, which may be in the form of a bicycle having a frame 11 and a pedal-crank assembly 12 which rotates relative to the frame 11. The pedal-crank assembly includes a crank wheel 13 and a left crank arm 14 and a right crank arm 15 affixed thereto so that the user is able to rotate the crank arms in either direction. In one embodiment, the crank wheel 13 is a chain wheel coupled by a chain 16 to a smaller sprocket 17 that drives the ground-engaging rear wheel 18 of a moving bicycle and in an alternative embodiment shown in FIG. 2, a stationary bicycle/ergometer has the pedal-crank assembly 12 coupled via chain 16 and sprocket 17 to a suitable load 21 that can be varied according to the user's selection.

The apparatus will now be described generally with reference to the schematic diagram of FIG. 1 followed by a more detailed description of specific features of construction.

A torque measuring device 25 is mounted on the pedal-crank assembly 12 to rotate conjointly therewith and produces electric signals proportional to the torque generated by the user. A temperature sensor 22, also mounted on the pedal-crank assembly 12, provides electrical signals proportional to temperature. A signal transfer device 26 transfers electric signals from the rotating pedal-crank assembly 12 to a selected non-rotating part of frame 11 of the power-using device 10. The torque signals from torque measuring device 25 and temperature signals from temperature sensor 22 are in analog form and are applied via signal transfer device 26 to an analog to digital converter 30 to provide corresponding digital signals for use by a microprocessor 31. An angular position sensor 27 associated with the pedal-crank assembly 12 provides electric signals indicating selected angular positions of the pedal-crank assembly. A wheel rotation sensor 20 provides digital signals proportional to distance traveled (where applicable). A heart beat sensor 33 provides heart beat signals as generated by user. A timer 32 provides electric signals proportional to real time. The microprocessor 31 has a program ROM 35 and a RAM 36 coupled thereto. There is further provided control keys 37 (mode, start/stop, reset) for user control of functions. A display device 38 displays the various data from the microprocessor 31 and a sound device 39 provides audible signals to the user.

The programmed microprocessor 31 receives the signals from sensors 20, 27 and 33, converter 30, and timer 32 and manipulates and/or stores this data as well as performs several computations. Signals from the control keys 37, as operated by the user, determine which of the various parameters are sent to the display device 38. The flowchart for the program of the microprocessor 31 is illustrated in FIGS. 3 and 3A.

Generally, an analog voltage signal, which is proportional to the torque generated by the user, at the output of torque measuring device 25 is produced by strain gauges mounted on load-carrying elements of the rotating pedal-crank assembly 12. Three configurations of the strain gauge placement are described below.

The first is an arrangement for measuring the resultant or net torque of the left plus right legs of the user of the pedal-crank assembly. Strain gauges are mounted on a selected element between the output drive assembly (crank wheel 13) and the right crank arm 15. FIG. 14 shows strain gauges 56 mounted on torque link 52 which will be described more fully hereinafter.

The second arrangement is identical to the first with the addition of more strain gauges selectively mounted on the right crank arm 15. The additional strain gauges 56A are shown in FIG. 12. In addition to the resultant torque measured in the first arrangement, the torque from the right leg only can be measured.

The third arrangement is shown in FIG. 7 with strain gauges 56B mounted on both the left crank arm 14 and the right crank arm 15. Both left and right torques can be measured separately by this arrangement.

The output torque to the crank wheel 13 is the algebraic sum of the torques applied to the right and left crank arms:

$$T \text{ (output)} = T \text{ (right)} + T \text{ (left)} \qquad \text{(Equation 1)}$$

Thus, while the said first arrangement is measuring only one torque, namely the resultant of the left plus right, both said second and third arrangements are measuring two torques. In the second arrangement, the resultant (output) torque and the right torque are measured separately, and thus, the left torque can be determined by subtracting the right value from the resultant torque value. The third arrangement measures left and right torques separately, and thus, the resultant (output) torque can be determined by adding left and right values.

While the first arrangement allows measurement of the resultant torque, only the second and third arrangements allow measurements of the torque that each leg is producing independently. The significance of this will be explained hereinafter.

FIG. 6 shows a typical Wheatstone bridge circuit arrangement of strain gauges for measuring singular torque values. A fixed DC voltage V+ is applied across the two branches having resistance elements A and D in series and B and C in series. Each of these elements A, B, C, and D may be individual resistance strain gauges mounted at selected positions on the pedal-crank assembly or torque link as described hereafter. The voltages V1 and V2 at the output of the bridge are applied to the differential inputs of an operational amplifier 57 to obtain an amplified voltage signal which is proportional to the torque produced on the pedal-crank assembly by the user. The circuit is shown to have a feedback resistor 75 connected between the output of amplifier 57 and terminal V1 and a resistor 76 connected between terminal V2 and ground. These resistors determine the amplification ratio of the operational amplifier 57. It is also possible to use only one or two active strain gauges in the circuit, e.g. A, or A and B, and to use fixed resistors for the remaining elements.

Two separate circuits as described above with reference to FIG. 6 are used to provide signals when two torques are measured as is the case with FIGS. 7 or 12 or 15.

All of the above discussed elements used in connection with measuring torque are mounted on the pedal-crank assembly 12 and rotate with it and are arranged to provide torque signals at any angular position.

The temperature sensor 22 preferably is mounted on the rotating pedal-crank assembly 12 to provide an electrical signal proportional to the temperature which is used to establish a temperature correction factor for the torque measuring circuitry as well as to determine the actual temperature.

The signal transfer device 26 is the means for transferring the electrical signals from the torque measuring and temperature measuring circuits on the rotating pedal-crank assembly 12 to stationary circuits on the frame 11. One suitable arrangement is to have circular conductive rings and "brush" contactors which can be arranged in two ways: first, with the conductive rings selectively mounted on the rotating pedal-crank assembly and the "brushes" mounted on the frame; or second, with the rings mounted on the frame and the "brushes" selectively mounted on the rotating pedal-crank assembly. This form may further be arranged to provide the necessary voltages for the strain gauges, temperature sensor, and associated operational amplifiers from a single battery 44. Battery 44 is shown to supply power via device 26 over line 41 to sensor 22 and device 25. This is not necessary when voltage is provided by battery 44a discussed hereafter. Battery 44 also supplies power to the microprocessor 31 and other devices in housing 40. Other arrangements of transfer devices 25 which are "wireless" include optical, radio frequency, or ultra-sonic transfer means.

Generally, electrical signals are produced by the angular position sensor 27 which indicate when the pedal-crank assembly 12 is at each selected equiangular position as it is rotated by the user. Typically, an equiangularly encoded disk rotates with the pedal-crank assembly, and a detector means, mounted on the frame 11, produces electrical signals corresponding to each equiangular position of said pedal-crank assembly. Typically, there will be sixteen equiangular positions determined by said sensor, i.e. every 22.5 degrees. (The angular position sensor is a "shaft encoder.") Five configurations of signal outputs are:

1. A single channel system which indicates every equiangular increment only (no means to determine direction of rotation or specific position, only change of position); one signal=$d\theta$.

2. Number 1 plus one specific position, e.g. "TOP" (one specific position and every equiangular change of position are known but not the direction of rotation); two signals=$d\theta$ and $\theta$.

3. A two channel system which gives signals which alternate from one channel to the other as it is rotated in one direction (thus direction of rotation is known); two signals=$d\theta 1$ and $d\theta 2$.

4. Number 3 plus one specific position, e.g. "TOP" (thus one specific position and the direction of rotation are known); three signals=$d\theta 1$, $d\theta 2$ and $\theta$.

5. Multi-channel, "absolute" position which produces binary or Grey coded signals (always know position and direction of rotation); requires four signals to determine sixteen positions which is the minimum number of divisions used; four signals=$\theta 1$, $\theta 2$, ... $\theta 16$.

The equiangularly encoded disk and sensor actuation system may be one of the following four methods:

1. Optical, using an infrared emitter/detector pair using either:
   A. A slotted disk which cuts or does not cut the light beam going from the emitter to the detector;
   B. A reflective/non-reflective disk which reflects or does not reflect the light beam from the emitter to the detector.

2. Magnetic, with multiple magnets mounted equiangularly which actuate reed switches or Hall-effect sensors, or which generate electrical pulses when their magnetic fields cut through a pick-up sensor coil 3. Variable reluctance, with rotating, equiangular lobes which produce zero-crossing voltages.

4. Mechanical, using:
   A. micro-switches actuated by equiangular cams.
   B. "Brushes" contacting a conductive/non-conductive equiangular "toothed" disk.

A singular, specific-position electrical signal for signal configurations 2 and 4 above may be provided with any singular implementation of any of the above actuation methods.

The electrical signals from the angular position sensor 27 are sent to the microprocessor 31 and are conditioned to provide acceptable signals for it using a Schmidt trigger.

When the measuring apparatus of the present invention is attached to a bicycle having a driven wheel, a wheel rotation sensor 20 may be selectively applied to provide electrical signals which provide data for determining values relating to distance, speed and acceleration. The simplest arrangement is to have a magnet attached to the rotating wheel, e.g. on a spoke, and to have a reed switch or Hall-effect sensor attached to the frame of the bicycle. Each time the magnet passes the switch or sensor, a signal is sent to the microprocessor 31 signifying that the bicycle has traveled some calibrated distance. Multiple magnets arranged equiangularly on the rotating wheel 18 may be used to provide a higher degree of accuracy for measuring the distance.

Signals from the user's heart beats are sensed by the heart beat sensor 33 by either a chest-mounted belt with selectively placed electrodes which detect actual electrical heart signals (EKG) or an "earlobe" type of blood-flow detector. The signals are amplified and conditioned as necessary, then sent to the microprocessor 31 by either wires or electromagnetic waves. In addition to providing ordinary heart rate data, the combination of several parameters by the microprocessor provide unique values for measuring and evaluating the efficiency and physical conditioning level of the user.

The timer 32 preferably is a quartz-based oscillator which will provide accurate real-time, electrical signals for determining various time intervals as required by the microprocessor program, such as the time interval for one complete revolution of the pedal-crank assembly and for a user-controlled "stop-watch" time interval.

A preferred arrangement utilizes the same oscillator that is used for the microprocessor "clock". It is further preferred that the microprocessor 31 be of a type that has a free-running counter which is continually being incremented by the oscillator and which can be "captured" in a "timer" register by an input trigger signal such as that from the angular position sensor for determining the "TOP" position of the pedal-crank assembly. Trigger signals are used to determine a time interval as follows: when the first trigger signal occurs, the microprocessor "captures" some value of the counter in a "timer" register; this value is saved in a particular memory register; when the second trigger signal occurs, the microprocessor "captures" the new value of the counter in the "timer" register; to obtain the value for the time interval between the first and second trigger signals, the first counter value is subtracted from the second counter value, and this value is saved in another memory register; finally, the "timer" value for second trigger is saved in the particular memory register used for this purpose in order for it to be available for determining the next time interval.

An alternative arrangement for the timing system is to have a "start-stop-read-zero" configuration. The value of a time interval is determined as follows: a trigger signal stops the clock, sends the time value to the microprocessor, sets the clock back to zero, then starts the clock again. This process is repeated every time a trigger signal is sent to the timer. Besides having much more complicated circuitry, this system always "loses" a small time interval between the time when the clock is stopped and when it is restarted.

The analog to digital converter 30 provides the microprocessor 31 with digital electrical signals, which it requires for processing, from the analog electrical signals of the torque measuring device 25 and the temperature sensor 22. The converter 30 may be separate from the microprocessor but is preferably integral with it, thus reducing the complexity of the circuitry and programming. Multi-channel inputs are also preferred over a multiplexed single-channel input for the same reason. A conversion time on the order of 25 microseconds is preferred to insure accurate measurements of the torques on the rotating pedal-crank assembly.

Typically, the operation is as follows: a control signal is sent to the converter 30 when a conversion is desired, e.g. from the angular position sensor 27; after its conversion delay, the converter 30 then provides a digital value proportional to the analog voltage it was sampling at the time the conversion signal was received; this value is then processed by the microprocessor 31.

Within a housing 40, the user is provided with several control keys 37, a visual display 38, and audible device 39 as means to utilize and control the apparatus. The housing 40 will normally be mounted so as to be easily seen and reached by the user and will normally contain the microprocessor 31, battery 44, additional circuitry, control keys 37, display 38 and sound device 39.

Control keys 37 may include such controls as: an "ON/OFF" switch for controlling the power to the entire apparatus, a "RESET" switch for "zeroing" and/or restarting the apparatus, a "MODE" switch for selecting which mode or function is to be utilized and/or displayed for the user, a "START/STOP" switch for starting and stopping certain functions which are user-controlled, a "SET" switch which will enable the user to "set" certain constants such as wheel size or maximum heart rate for alarm signals, and "ALARM" for enabling or disabling alarm functions.

The display 38 is an important part of the apparatus in terms of informing/updating the user with actual data regarding output parameters. Typically, display 38 will consist of a liquid crystal display (LCD) device which can display at least four decimal digits, but which preferably can display alpha-numeric characters as well. A custom LCD with indicators for each of the operating modes and with the capacity to display two, four digit numbers is preferable. An alternate arrangement which also allows a graphical display of certain data, e.g. torque vs. crank angle, may be used with a complex version of the apparatus. Alternatively, the display 38 may consist of appropriate light-emitting-diode (LED), cathode-ray-tube (CRT), or print-out devices.

A piezo-crystal, a speaker or a buzzer device may be used for the sound device 39 which provides the user with an additional form of data. It may provide an indication of a successful input key signal or that a certain preset value has been reached or exceeded, e.g. maximum power level or exercise time period. The actual sounds may be simple tones or synthesized speech.

The microprocessor 31 utilizes, processes, controls and stores all signals and data which are input and output while operating said apparatus. The "read-and-write memory" (RAM) 36 and the "read-only memory" (ROM) 35 are preferably integral with microprocessor 31, but may be separate. As described above, it is preferable to have the analog to digital converter 30 and the timer 32 integral with the microprocessor 31, but these devices may be separate. If all the above mentioned devices are integral with said microprocessor, then it may be referred to as a microcontroller.

The microprocessor 31 is both a "hardware" and "software" device in that it is necessary to provide power (from battery 44) and electrical connections for all the above described signals, i.e. "hardware", and further to provide a "software" program within the ROM 35 consisting of a logical sequence of binary-coded, machine language commands. The "hardware" portion has been described above, and now the theoretical basis for the "software" will be explained.

All measurements relating to Work, which is herein defined as Force multiplied by Distance, with the apparatus of the present invention are based on the formula relating work as a function of torque and angle of rotation:

$$\text{Work} = \int_a^b T\, d\theta \qquad \text{(Equation 2)}$$

where T is an instantaneous torque value and a and b are the beginning and ending angles of rotation, respectively. This formula is particularly applicable to a user rotating a pedal-crank assembly because the values of the torque generated vary greatly around 360 degrees of motion. FIG. 4 shows a graph of typical torque values for the resultant of left plus right legs vs. angle of the pedal-crank assembly. FIG. 5 shows a similar graph, but with separate curves for the left and right legs. The torque values are different for right and left legs, and the values for the left leg are negative for the first 180 degrees and positive for the next 180 degrees. The right torque values are essentially just the opposite of the left. Finally, if the values for left and right are added, the curve of FIG. 4 will result, which is simply an application of Equation 1.

Equation 2, shows that integrating the values of torque over an angle from 0 to 360 degrees gives the work over one revolution, which is the same as the area under the curve in FIG. 4. FIG. 5 shows that, integrating the left torque values from 0 to 180 degrees gives a negative value for the work shown by the area below the x axis; integrating the right torque values over the same angle gives a positive value shown by area above the x axis. It is apparent that one leg is doing work against the other, not just against a load. By measuring separate torque values, it is possible to evaluate the proportion of work done by each leg, which can be of considerable importance in athletic training or rehabilitation.

While Equation 2 gives an exact value for work, a very good approximation can be made by applying an approximate-integration formula such as the "Trapezoidal Rule". For sixteen equiangular measurements of the torque over one complete revolution, i.e. every 22.5 degrees, the Trapezoidal Rule may be written as:

$$\text{Work (per revolution)} = \pi \div 16 \, \Sigma(T_0 + 2T_1 + 2T_2 + \ldots + 2T_{15} + T_{16}) \quad \text{(Equation 3)}$$

where $T_0$ = torque at 0 degrees, $T_1$ = torque at 22.5 degrees, $T_2$ = torque at 45 degrees, etc. . . . , and $T_{16}$ = torque at 360 degrees.

Thus, by measuring torque at 0 degrees, preferably when the right crank arm is in the vertical "TOP" position, and adding twice the torque at 22.5 degrees, twice the torque at 45 degrees, etc., twice the torque at 337.5 degrees, and the torque at 360 degrees, a value is obtained which, multiplied by the appropriate constant, is the value for the work over one complete revolution.

Power is defined as work per unit time:

$$\text{Power} = \text{Work} \div \text{Time} \quad \text{(Equation 4)}.$$

Dividing the value of the work done in one revolution by the value of the time required for the revolution yields a value for the power produced.

The "hardware" previously described can provide all the necessary electrical signals to determine the work done and the power produced over a selected angle of rotation.

A simplified version of the Trapezoidal Rule, which actually determines the average value when applied to only two points, may be used to determine a value for the work over every equiangular interval, e.g. 22.5 degrees. The formula for this form is:

$$\text{Work} = \pi \div 16 \, (T_0 + T_1) \quad \text{(Equation 5)}$$

This form is useful when the heart beat sensor is used, and a value for the work per heart beat is desired.

Another formula which may be used for the approximate integration process is Simpson's Rule (Prismoidal Rule), which may provide a more accurate result.

The flowchart (FIGS. 3 and 3A) is simplified and general. It will produce a display of the POWER, MAX POWER, and WORK simultaneously after each revolution of the cranks. The units of the displayed values will be determined by the calibration of the torque signals, the interval timer units, and the constants A and B. There is no reference to which torque signal is being read, and it can apply to left, right, or both sides combined. The torque signal is a calibrated, analog voltage which is proportional to the torque exerted on said crank arms.

Because of the simplification of this flowchart, the following items should be noted: there is no provision for determining whether the pedal-crank assembly has been rotated continuously in one direction; storing the torque values at the various angles and comparison for maximum torque is not shown; normally, there would be additional programming to allow a MODE key to select various read-outs; the Trapezoidal Rule algorithm for approximate integration is shown which can be modified to utilize Simpson's Rule.

Referring to the flowchart of FIGS. 3 and 3A, the terms are defined as follows: 'TOP' means the right crank arm is in the vertical position; 'CLEAR' means erase or set equal to zero; 'TEMP. WORK' means temporary work or a value which is accumulated over the selected integration angle; 'MAX POWER' means maximum power; 'dt' means the value of the time interval between the starting and stopping of the interval timer for the selected revolution; '$T_0$' means the torque reading at the 'TOP' position; '$T_n$' means the torque reading at the "nth," equiangular displacement position; 'STORE' means "save the value in memory."

The main loops which check for signals from the angular position sensors and the reset key are shown as "polling loops"; it may be preferable to use "interrupts" to control the program flow when possible.

The parameters which can be determined using appropriate software algorithms include the following:

Torque produced on pedal-crank assembly (in units of pound-feet, etc.) with values for maximum, minimum, average and selected angles of crank-arm positions;

Work (in units of foot-pounds, kilopond-meters, calories, etc.) as it is performed with a summation of the total;

Power (in horsepower, watts, calories per minute, kilopond-meters per minute, etc.) with values for instantaneous, maximum and average;

Time (in hours, minutes, and seconds) with values for a selected interval or time of day;

Crank Rotation with values for total number of revolutions, instantaneous revolutions per minute (RPM), maximum RPM, and average RPM;

Wheel Rotation (where applicable) with values for distance (in miles, kilometers, etc.), speed (in MPH, KPH, etc.) with values for instantaneous, maximum and average, and acceleration (in feet per second per second, "g", etc.) with values for instantaneous and maximum;

Work per Distance (in pounds-force, grams-force, etc.) with instantaneous, average or maximum values;

Heart Beats with values for total number of beats, instantaneous beats per minute (BPM), maximum BPM, and average BPM;

Work per Heart Beat (in foot-pounds per beat, calories per beat, kilopond-meter per beat, etc.) with values for instantaneous, maximum, and average; and Temperature (in degrees Fahrenheit or Celsius).

The parameters of Torque, Work, and Power may be further divided into values which are determined separately for the right and left legs.

The units of the parameters may be user-selectable by applying appropriate constants within the program, e.g. select watts or horsepower, or foot-pounds or calories.

The user may be able to set limits for parameters with a means to alert the user that limits have been reached or exceeded. The various parameters may be selectively displayed by the user by means of a mode-select control key.

Referring now to FIGS. 8–15, there is shown a bicycle with a pedal-crank assembly 12 on which there is installed a measuring apparatus according to the present invention. The apparatus includes several parts mounted at different locations on the bicycle as will be described in detail hereinafter. The bicycle shown has the usual frame 11, seat 42, handle bars 43, front wheel 46 and rear wheel 18. A pedal-crank assembly 12 includes the crank wheel assembly 13, the crank axle 48, left and right crank arms 14 and 15, respectively, connected thereto, having left and right pedals 45 and 47, respectively, attached to the ends of said left and right crank arms. A chain 16 extends around the crank wheel assembly 13 and a rear sprocket 17 so that when the user rotates the pedal-crank assembly 12 by pedaling, torque is transmitted to the rear wheel 18 to propel the bicycle.

A housing 40 is shown in FIG. 17 as mounted on the handle bars 43 and has a display 38 (LCD) and control keys 37 within the access and view of the user. The housing 40 contains the apparatus illustrated in block form in FIG. 1.

The pedal-crank assembly 12 shown in FIGS. 8-15 is of a special type which is constructed with the crank wheel assembly 13 rotatable relative to the crank axle 48. The left and right crank arms 14 and 15 are affixed to said crank axle. The chain wheel mounting flange 49 is affixed to the outside of bearing 50, the inside of which is affixed to hub 51 on the right crank arm 15, thus allowing said rotation between 13 and 48. A torque link 52 is connected between a drive pin 53 on said right crank arm and one of the screw fasteners 54 which attach the chain wheels 55 to the mounting flange 49. Link 52 thus transmits all the torque generated by the user on the pedals to the chain wheel having chain 16 connected to it. Strain gauges 56, mounted on said link and connected to operational amplifier 57 and battery 44 as shown in FIG. 6, produce an analog voltage signal proportional to the net torque generated by the user.

The strain gauge elements are shown in FIG. 14 on the torque link 52 with elements A and C extending along the link 52 and opposite one another and elements B and D extending transverse of the link and opposite one another.

In a second embodiment, strain gauges 56A are mounted at selected positions on the right crank arm 15 and are connected to a second circuit as shown in FIG. 6 so as to produce a second analog voltage signal proportional to the torque produced by the user only on said right crank arm.

A third embodiment (shown in FIG. 7) consists of strain gauges 56B mounted at selected positions on both left and right crank arms 14 and 15; dual circuits as shown in FIG. 6 provide two separate analog voltage signals which are proportional to the left and right torques generated by the user.

The strain gauge elements are shown in FIG. 7 on each crank arm with elements A and C disposed side by side extending along the top of the crank arm and elements B and D disposed side by side along the bottom of the crank arm. Element B is shown opposite element A and element C is shown opposite element D.

Temperature sensor element 58 in FIG. 12 is shown mounted on the pedal-crank assembly and provides an analog voltage signal proportional to the temperature as shown in the circuit of FIG. 16. The circuit for sensor 22 has a temperature sensor element 58, preferably an LM335, with a resistor R1 connected in a series circuit therewith and a voltage V+ applied to this series circuit. A variable resistor R2 is connected across element 58 with a tap of the resistor R2 connected to element 58. The output of the circuit is at the point resistor R1 connects to element 58. The output signal from the circuit is used for temperature corrections of torque signals and for reading temperature.

The signal transfer device 26 shown in FIG. 10 couples the torque and temperature measurement electric signals from the operational amplifiers 57 on the rotating crank wheel to devices on the frame 11. The signal transfer device 26 shown in FIG. 10 includes a circuit board 61 mounted to rotate with the pedal-crank assembly 12. The circuit board has multiple concentric electrically conductive rings 62. The output terminal from each operational amplifier (FIG. 6) is connected to a specific ring. Separate brushes 63, selectively mounted on the frame, contact each ring so that the electric signals from the operational amplifiers are transmitted through the conductive rings, through the brushes and by electric wires to housing 40 for use by circuits therein.

Two conductive rings and corresponding brushes are used to provide a common ground and to supply the rotating circuitry with a supply voltage V+ from battery 44, which is contained in housing 40. An alternative embodiment has a second battery 44A mounted on the rotating pedal-crank assembly which supplies voltage V+ as required by the rotating circuitry.

The angular position sensor shown in FIGS. 8-15 is of the Number 2 type previously described and consists of two sensor devices: one to signal that the right crank arm 15 is at the vertical position (TOP) and another sensor device to signal that said crank arm is at one of the selected equiangular positions, i.e. every 22.5 degrees.

A crank arm vertical position (TOP) sensor 64 is shown mounted on the frame 11 and its activator is mounted on the rotatable pedal-crank assembly. As seen in FIG. 11, sensor 64 includes a reed switch 65 mounted on said frame and a permanent magnet 66 mounted on circuit board 61 such that when the rotatable crank arm is at the TOP position, a signal is generated as the switch is activated by the magnet.

The second angular position sensor 67 is shown mounted on the bicycle frame 11 and its activator, mounted on the rotatable crank axle 48, is a slotted disk 68 with a plurality of equiangular, circumferentially spaced slots, e.g. sixteen. The sensor 67 has an infrared emitter/detector assembly supported by said frame and which includes an LED beam emitter 69 which sends a light beam toward a beam detector 70. The electric circuit diagram of FIG. 18 shows the LED beam emitter 69 connected in a series circuit with resistor R3 and the beam detector 70 connected in a series circuit with resistor R4. These two series circuits have a voltage V+ applied thereto. An output line taken at the collector and at resistor R4 is applied to a Schmidt trigger 73. The sensor 67 and disk 68 are selectively arranged so that the disk will alternately cut and not cut the beam as it is rotated, thus generating electric signals as each equiangular slot passes the light beam.

An optional embodiment for the above second angular position sensor 67 consists of having the beam from the emitter 69 arranged so that it will be reflected or not reflected from the equiangularly encoded disk to the beam detector 70 as said disk rotates; electric signals are generated in a manner similar to that of the previous paragraph.

The signals from the two angular position sensors 64 and 67 are conditioned by Schmidt triggers before being fed to the microprocessor 31. Power for the sensors is provided by battery 44.

A magnet 71 is shown mounted at a selected position and location on a spoke of the rear wheel 45 such that once every wheel revolution, reed switch 72 is activated providing an electrical signal indicating that a distance of one wheel circumference has been traveled.

A multiple-electrode, heart EKG sensing device 33 is selectively mounted on the user's chest to provide heart beat signals to microprocessor 31 for determining various heart-rate parameters. A preferred embodiment for device 33 uses electromagnetic waves to transmit the conditioned heart beat signals, as generated by the user, to a receiving device located in housing 40. However, use of small, flexible wire to transfer said heart signals is preferable from an economic standpoint. A heart beat sensor which utilizes a small light source and detector system to sense blood flow and which is selectively held onto the user's ear lobe, is also adaptable for providing signals for heart-rate parameters.

The preferred embodiment is for the timer 32, the analog to digital converter 30, the ROM 35, the RAM 36 and the microprocessor 31 to be a single integrated circuit device, such as the Motorola HCMOS microcontroller MC68HC11A2. While use of such a microcontroller is preferable for minimizing the circuitry and software, the same operations can be performed by separate devices for each of the functions.

From the foregoing, it is apparent that the specific program for the microprocessor will depend on the specific hardware connections, the capabilities of the microprocessor itself, and the particular parameters chosen to be evaluated. However, the flowchart of FIG. 3 shows a basic algorithm for utilizing signals for torque, angular position, and time to determine values for work, power, and maximum power. Additionally, input signals from a wheel sensor, a heart beat sensor and a temperature sensor may be integrated into the program to provide additional data relative to distance, speed, heart rate, work per heart beat and temperature. User-controlled key inputs may be programmed to provide selection and control of program functions, display data and units.

From the foregoing, it is further apparent that the present invention provides a small, battery-powered, microprocessor-controlled, measuring apparatus which can be adapted to any power-using device having a pedal-crank assembly rotated by a user and which will display a variety of output parameters enabling the user to evaluate his or her performance in many ways.

Although the present invention has been described with a certain degree of particularity, it is understood that the present disclosure has been made by way of example and that changes in details of structure may be made without departing from the spirit thereof.

What is claimed is:

1. Apparatus for measuring selected output parameters of a user of a power-using device comprising:
    a power-using device having a frame and a pedal-crank assembly with relative rotation between said pedal-crank assembly and said frame being provided by the user,
    torque measuring means mounted on said pedal-crank assembly providing first plurality of electric signals proportional to torque generated by said user in rotating said assembly,
    angular position sensing means providing second plurality of electric signals indicating selected angular positions of said assembly as said assembly is rotated by the user, said angular positions being equiangular,
    timing means providing third plurality of electric signals proportional to real time,
    transfer means for transferring said first electric signals between said rotating assembly and a programmed microprocessor means on said frame,
    said programmed microprocessor means on said power-using device and responsive to said first, second and third signals and for:
        determining a value of torque at each of said equiangular positions as said assembly is rotated by said user and in response to said first and second electric signals,
        determining a value of a time interval between two selected angular positions of said assembly as said assembly is rotated by the user in response to said second and third electric signals,
        performing an approximate integration of said values of torque over said two selected angular positions to provide a value of work done by the user in rotating said assembly through said two selected angular positions,
        dividing said value of work by said value of the time interval to provide a value of power provided by said user during said time interval, and
    readout means on said power-using device responsive to outputs from said programmed microprocessor means to display said torque, work and power values.

2. Apparatus as set forth in claim 1 wherein said power-using device is a movable bicycle having a frame on which said pedal-crank assembly is mounted for rotating a ground-engaging wheel of the bicycle.

3. Apparatus as set forth in claim 1 wherein said power-using device is a stationary device having a frame on which said pedal-crank assembly is mounted for rotating a load device to apply a selected load to said assembly.

4. Apparatus as set forth in claim 1 wherein said torque measuring means includes strain gauge means connected to said assembly to provide a measure of total torque applied to said assembly by the user.

5. Apparatus as set forth in claim 4 wherein said assembly includes a crank wheel and crank axle movable relative to one another and includes strain gauge means mounted on a torque arm connected between said crank wheel and crank axle.

6. Apparatus as set forth in claim 4 including amplifier means to amplify output signals of said strain gauge means.

7. Apparatus as set forth in claim 4 wherein said strain gauge means includes a Wheatstone bridge having two branches across which a voltage is applied, a fixed resistor in each branch and a second resistor in each branch in series with an associated fixed resistor, each said second resistor having a resistance that varies with the torque applied to said assembly, said bridge having a differential voltage at connections between said fixed resistors and said second resistors that varies in relation to said applied torque.

8. Apparatus as set forth in claim 5 wherein said pedal-crank assembly includes a right crank arm and said torque measuring means includes a second strain gauge means connected to said right crank arm to provide a measure of torque applied to the right crank arm by the user and a measure of torque applied to a left crank arm as a result of subtracting the torque applied to the right crank arm from the total torque.

9. Apparatus as set forth in claim 5 wherein said strain gauge means includes a Wheatstone bridge having two branches across which a voltage is applied, a fixed resistor in each branch and a second resistor in each branch in series with an associated fixed resistor, each said second resistor having a resistance that varies with the torque applied to said assembly, said bridge having a differential voltage at connections between said fixed resistors and said second resistors that varies in relation to said applied torque.

10. Apparatus as set forth in claim 1 wherein said assembly includes a right crank arm and a left crank arm and said torque measuring means includes a right strain gauge means connected to a right crank arm and a left strain gauge means connected to a left crank arm to provide a measure of torque of each of said crank arms and a measure of total torque by adding the torque applied to the left and right crank arms.

11. Apparatus as set forth in claim 8 or 10 wherein each of said strain gauge means includes a Wheatstone bridge having two branches across which a voltage is applied, a fixed resistor in each branch and a second resistor in each branch in series with an associated fixed resistor, each said second resistor having a resistance that varies with the torque applied to said assembly, said bridge having a differential voltage at connections between said fixed resistors and said second resistors that varies in relation to said applied torque.

12. Apparatus as set forth in claim 1 including a temperature sensor means responsive to temperature at said assembly providing electric signals proportional to temperature.

13. Apparatus as set forth in claim 12 including an analog to digital converter converting said electric signals proportional to temperature which are analog in form to corresponding binary digital electric signals.

14. Apparatus as set froth in claim 1 wherein said angular position sensing means includes a disc with a plurality of equiangular slots, said disc rotating with said assembly with said slots arranged to interrupt a beam of an emitter directed toward a detector which generates corresponding electric signals.

15. Apparatus as set forth in claim 1 wherein said angular position sensing means includes a top position crank arm sensor to signal a crank arm is in a top position and another crank arm sensor to signal that said crank arm is at each of said selected angular positions.

16. Apparatus as set forth in claim 1 wherein said timing means includes a quartz-based oscillator operating at a selected frequency.

17. Apparatus as set forth in claim 1 including an analog to digital converter converting said first electric signals which are analog in form to corresponding binary digital electric signals. including an analog to digital converter converting said electric signals proportional to temperature which are analog in form to corresponding binary digital electric signals.

18. Apparatus as set forth in claim 1 wherein said transfer means includes circular conductive rings and brush contactors mounted on said frame and said assembly.

19. Apparatus as set forth in claim 1 wherein said programmed microprocessor means includes a programmed microcontroller.

20. Apparatus as set forth in claim 1 wherein said programmed microprocessor means has a programmed ROM and a RAM for data storage.

21. Apparatus as set forth in claim 1 including a DC battery providing power for said microprocessor means.

22. Apparatus as set forth in claim 1 including a manually operable keyboard control coupled to said microprocessor means.

23. Apparatus as set forth in claim 22 wherein said keyboard control includes an on/off switch for controlling power, a reset switch for zeroing, a mode switch for selecting a function, a start/stop switch for starting and stopping selected functions, a set switch to select constants and an alarm switch for enabling and disabling alarm functions.

24. Apparatus as set forth in claim 1 wherein said equiangular positions are sixteen in number at 22.5 degree intervals.

25. Apparatus as set forth in claim 24 wherein said approximate integration is according to a Trapezoidal Rule:

$$\text{Work (per revolution)} = \pi \div 16 \; \Sigma(T0 + 2T1 + 2T2 + \ldots + 2T15 + T16)$$

where $T0$ = torque at 0 degrees, $T1$ = torque at 22.5 degrees, $T2$ = torque at 45 degrees, etc. . . . , and $T16$ = torque at 360 degrees.

26. Apparatus as set forth in claim 1 wherein said readout means includes a visual display.

27. Apparatus as set forth in claim 1 and additionally including user heart beat sensor means providing electrical signals coupled to said microprocessor means for determining heart rate data of the user including work per heart beat values.

28. Apparatus as set forth in claim 1 and additionally including wheel rotation sensor means providing electrical signals coupled to said microprocessor means for determining distance data in conjunction with work, power and time values.

29. Apparatus as set forth in claim 1 including an audible device responsive to an output from said microprocessor means.

30. Apparatus for measuring and displaying torque, work and power values of a user of a power-using device comprising:

a power-using device having a non-rotating frame member and a pedal-crank assembly with relative rotation between said pedal-crank assembly and said member being provided by the user, a torque measuring device mounted on said pedal-crank assembly providing first plurality of electric signals proportional to torque generated by said user in rotating said assembly, an angular position sensing device providing second plurality of electric signals indicating selected angular positions of said assembly as said assembly is rotated by the user, said angular positions being equiangular, timing means providing third plurality of electric signals proportional to real time, transfer means for transferring said first electric signals between said rotating assembly and a programmed microprocessor means on said member, said programmed microprocessor on said power-using device and responsive to said first, second and third signals for:

determining a value of torque at each of said equiangular positions as said assembly is rotated by said users and in response to said first and second electric signals, determining a value of a time interval between two selected angular positions of said assembly as said crank wheel is rotated by the user in response to said second and third electric signals, performing an approximate integration of said values of torque over said two selected angular positions to provide a value of work done by the user in rotating said assembly through said two selected angular positions, dividing said value of work by said value of the time interval to provide a value of power provided by said user during said time interval, temperature sensor means responsive to the temperature at said assembly providing electric signals proportional to temperature, heart beat sensor means providing electric signals for determining heart rate data of the user including work per heart beat values, wheel rotation sensor means providing electric signals for determining distance in conjunction with torque, work, power, time and heart beat values, and a visual display on said power-using device responsive to outputs from said programmed microprocessor means to display said RPM, torque, work, power, time, distance and heart beat values.

* * * * *